United States Patent [19]

Morikawa et al.

[11] 4,205,193
[45] May 27, 1980

[54] PROCESS FOR PRODUCTION OF ISOPRENE CYCLIC TRIMERS

[75] Inventors: Hiroyuki Morikawa; Shooji Kitazume, both of Amimachi, Japan

[73] Assignee: Mitsubishi Petrochemical Company Limited, Japan

[21] Appl. No.: 927,982

[22] Filed: Jul. 26, 1978

[30] Foreign Application Priority Data

Aug. 3, 1977 [JP] Japan .................................. 52-93135

[51] Int. Cl.² .......................... C07C 3/10; C07C 3/21
[52] U.S. Cl. ................................... 585/367; 585/368; 585/507
[58] Field of Search .................... 260/666 B; 585/367, 585/368, 507

[56] References Cited

U.S. PATENT DOCUMENTS

| | | | |
|---|---|---|---|
| 3,076,045 | 1/1963 | Schneider et al. | 260/666 B |
| 3,214,484 | 10/1965 | Wittenberg et al. | 260/666 B |
| 3,758,621 | 9/1973 | Morikawa et al. | 260/666 B |

Primary Examiner—Veronica O'Keefe
Attorney, Agent, or Firm—Robert E. Burns; Emmanuel J. Lobato; Bruce L. Adams

[57] ABSTRACT

A process of the production of isoprene cyclic trimers, i.e., 1, 5, 9- and 1, 6, 9-trimethylcyclododecatriene-(1, 5, 9) through a catalytic oligomerization of isoprene by employing a catalyst prepared by a combination of a tri-valent titanium compound, an organoaluminum compound, an oxygen-containing compound such as carbonyl and ether compounds, and a compound such as a sulfur-containing compound and a nitrile compound.

7 Claims, No Drawings

PROCESS FOR PRODUCTION OF ISOPRENE CYCLIC TRIMERS

BACKGROUND OF THE INVENTION

This invention relates to a process for the production of 1, 5, 9- and 1, 6, 9-trimethylcyclododecatriene-(1, 5, 9) which are cyclic trimers of isoprene by a catalytic oligomerization of isoprene, and more particularly to a process for the production of isoprene cyclic trimers by employing a catalyst having improved characteristic features.

Heretofore, there have been a great number of patents and reports relating to studies on the production of each corresponding cyclic trimer by oligomerization of conjugated diene compounds with respect to butadiene, while relatively few reports on the study for such production of cyclic trimers with respect to isoprene are to be found.

Catalysts used for cyclic trimerization of isoprene may be classified broadly into the following three categories: A first group in which the Ti-based catalysts are employed has been proposed by the specifications of Japanese Patent Publication Nos. 2372/1960, 6170/1961, 17559/1962, 6468/1963, 14927/1963, 15375/1963, 29496/1970, 4456/1974, 4457/1974, 7154/1974, 7155/1974, 5933/1972, 7628/1973, 19303/1973, and 4215/1974, respectively. A second group in which Ni-based catalysts are adopted has been proposed by the specifications of Japanese Patent Publication Nos. 16882/1963, 14673/1964, 19156/1964, 22975/1968 and 31138/1975, Japanese Patent Laid-open Nos. 56950/1974, 56951/1974, 93941/1975, 68504/1976 and 98242/1976, respectively. A third group in which Cr-based catalysts are adopted has been proposed by the specifications of Japanese Patent Publication Nos. 5718/1961, 17559/1962, 6902/1974, 48307/1974 and 3054/1971, respectively.

In a process in which the Ni-based catalysts in the above-mentioned categories are employed, the catalyst concentration may be high, in general, and as a result, the yield based on the catalyst is low. There is also a great difference between the resultant cyclic trimers in their structures, i.e., a trans-trans-trans product is the principal component in the Ni-based catalysts, whilst a trans-trans-cis product is the principal product in the Ti-based catalysts. In a process in which the Cr-based catalysts are used, the catalyst concentration must be high similarly as in the case of the Ni-based catalysts, and as a result, the yield of trimethylcyclododecatriene based on the isoprene is low, i.e., less than 50%. Under the circumstances, when the process is carried out with a Ni- or Cr-based catalyst of a low concentration, its reaction velocity may be very slow, which requires much time for the process. The efficiency thereof may be inferior. These problems accompanying the use of these catalysts have been difficulties in industrial applications thereof. In the use of the Cr-based catalysts, a process for intensifying the catalytic activity by adding an aliphatic halo-compound has been proposed in Japanese Patent Publication No. 23377/1971. In this process, however, a by-product of a higher polymer which is adherent to a reaction vessel due to the aliphatic halo-compound may be produced easily.

On one hand, tetra-valent titanium compounds have been principally employed as Ti-based catalysts in conventional processes but have been accompanied by disadvantages such as the ease with which such tetra-valent titanium catalysts are poisoned by impurities such as moisture although these catalysts have high catalytic activities, and furthermore, a by-product of a higher polymer which is adherent to the reaction vessel is easily produced. Such a polymer which adheres to the reaction vessel is insoluble in a solvent and adheres to cooling coils and the like in the reaction vessel, thereby obstructing thermal conduction, and gives rise to troubles, so that it has been difficult to continuously carry out the reaction. In order to eliminate such difficulties as mentioned above, a process in which organoaluminum compounds are not used has been disclosed in the specification of Japanese Patent Publication No. 15375/1963. However, this process may be complicated because it requires pulverization with a ball mill at the time of a preparation of the catalyst.

In the above described three types of catalysts, the Ti-based ones can be considered to be advantageous because of their high activities. Accordingly, if the above described problem relating to the by-product of the polymer with adhesiveness to the reaction vessel, which has been frequently observed in the case where Ti-based catalysts are employed, can be solved, the above advantage afforded by the use of the Ti-based catalysts can be more favourably utilized.

SUMMARY OF THE INVENTION

It is an object of the present invention to solve the above described problems. This object can be achieved by the use of a modified catalyst containing a tri-valent titanium compound, which produces only a small quantity of the by-product of the vessel-adhering polymer, as its titanium component.

According to this invention, there is provided a process for producing isoprene cyclic trimers which, in the production of trimethylcyclododecatriene by a catalytic oligomerization of isoprene, is characterized in that the catalyst used for the process of this invention is prepared by a combination of the undermentioned compounds (A), (B), (C), and (D), respectively:

(A) a tri-valent titanium compound;
(B) an organoaluminum compound;
(C) an oxygen-containing compound selected from the group consisting of:
  (a) a carbonyl compound having the following formula

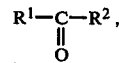

where $R^1$ is selected from the group consisting of $C_1$–$C_{10}$ alkyl, aryl, and aralkyl radicals; $R^2$ is selected from the group consisting of hydrogen, $C_1$–$C_{10}$ alkyl, aryl, aralkyl, and $OR^3$ groups wherein $R^3$ is selected from the group consisting of $C_1$–$C_{10}$ alkyl, aryl, and aralkyl radicals; and $R^1$ and $R^2$ may be combined with each other to form a cyclic structure; and (b) an ether compound having the following formula

where $R^4$ and $R^5$ each represents a member selected from the group consisting of $C_1$–$C_{10}$ alkyl, aryl, and aralkyl radicals; and $R^4$ and $R^5$ may be combined with each other to form a cyclic structure; and
(D) a compound selected from the group consisting of:
(a) a sulfur-containing compound having the following formula

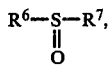

where $R^6$ and $R^7$ each represents a member selected from the group consisting of hydrogen, $C_1$-$C_{10}$ alkyl which may contain a thioether linkage in its chain, aryl, and aralkyl radicals; and $R^6$ and $R^7$ may be combined with each other to form a cyclic structure; and
(b) a compound having the formula

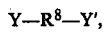

where Y and Y' each represents a member selected from the group consisting of CN, SCN, and $SR^9$ radicals wherein $R^9$ is selected from the group consisting of $C_1$-$C_{10}$ alkyl, aryl, and aralkyl radicals; and $R^8$ is selected from the group consisting of $-(CH_2)_n-$ wherein n is an integer having a value of 1-10,

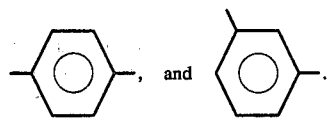

DETAILED DESCRIPTION OF THE INVENTION

In the process for production of isoprene cyclic trimers by a catalytic oligomerization of isoprene according to the present invention, the catalyst used for the process has principal characteristic features as fully described hereinbelow.

1. Catalyst

The catalyst comprises a combination of the compounds (A) through (D).

In the respective formulae of the above-mentioned compounds (A) through (D), $R^1$ through $R^7$ and $R^9$ may be the same or different members, respectively.

(1) Tri-valent titanium compounds (A)

As the tri-valent titanium compound, a tri-valent titanium halogen compound is preferable. Specific examples thereof are titanium trichloride, titanium tribromide, and titanium triiodide.

Furthermore, among tri-valent titanium compounds, there is one which is produced by a method wherein a tetra-valent titanium compound is reduced with lithium aluminum hydride, aluminum alkyl, or the like at room temperature. In this case, although aluminum halides are contained in the reduction products besides the tri-valent titanium compound, the reduction product may be used as such as the tri-valent titanium compound for the process according to the present invention with no additional step.

Reduction products which have been prepared by reducing a tetra-valent titanium compound with metallic aluminum at an elevated temperature and which are mixed crystals comprising a tri-valent titanium compound and an aluminum halide, such as $TiCl_3(A)$ or $3TiCl_3 \cdot AlCl_3$ by way of an example of a chloride, may also be used as the component (A) of the present invention as such or after having been activated by pulverization thereof, the activated product being, for example, $TiCl_3(AA)$ by way of an example of a chloride.

A tri-valent titanium halide can be used in the form of a complex with an appropriate electron donor, and, as the electron donor in this case, the catalyst component (C) or (D) according to the present invention may be used. Specific examples of complexes with titanium trichloride are benzaldehyde-titanium trichloride complex $[TiCl_3(C_6H_5CHO)_2]$, m-nitrobenzaldehyde-titanium trichloride complex $[TiCl_3(NO_2C_6H_4CHO)_2]$, cinnamaldehyde-titanium trichloride complex $[TiCl_3(C_6H_5CH=CHCHO)_2]$, acetonitrile-titanium trichloride complex $[TiCl_3(CH_3CN)_3]$, diethyl ketone-titanium trichloride complex $[TiCl_3 \cdot (C_2H_5COC_2H_5)_2]$, benzophenone-titanium trichloride complex $[TiCl_3(C_{13}H_{10}O)_2]$, dioxane-titanium trichloride complex $[TiCl_3(C_4H_8O_2)]$, and benzaldehyde-dimethyl sulfoxide-titanium trichloride complex $[TiCl_3(C_6H_5CHO).(CH_3SOCH_3)]$.

(2) Organoaluminum compounds (B)

As the organoaluminum compound, an aluminum compound having the general formula:

where R is selected from the group consisting of hydrogen, $C_1$-$C_{12}$ alkyl, aryl, and aralkyl radicals; X is a member selected from the group consisting of halogen atoms and OR' radicals (where R' is selected from the group consisting of $C_1$-$C_{12}$ alkyl, aryl, and aralkyl radicals); and n is a number selected from the values of 1, 1.5, 2 and 3, may be employed, and such aluminum compounds represented by the general formulae $AlR_2Cl$, $Al_2R_3Cl_3$, and $AlRCl_2$, respectively, are particularly preferable. Specific examples of these organoaluminum compounds are dimethylaluminum choride, ethylmethylaluminum chloride, diethylaluminum chloride, dipropylaluminum chloride, diisopropylaluminum chloride, dibutylaluminum chloride, ethylbutylaluminum chloride, diisobutylaluminum chloride, ethylchloroaluminum hydride, butylchloroaluminum hydride, dihexylaluminum chloride, dioctylaluminum chloride, diphenylaluminum chloride, dibenzylaluminum chloride, ethylaluminum sesquichloride, butylaluminum sesquichloride, isooctylaluminum sesquichloride, ethylaluminum dichloride, butylaluminum dichloride, and hexylaluminum dichloride.

Specific examples of the aluminum compounds having the general formula $AlR_n(OR')_{3-n}$, are dimethylmethoxy aluminum, diethylmethoxy aluminum, diethylethoxy aluminum, diethylphenoxy aluminum, dipropylethoxy aluminum, dipropylpropoxy aluminum, diisopropylmethoxy aluminum, dibutylethoxy aluminum, diisobutylbutoxy aluminum, dihexylethoxy aluminum, dicyclohexylisobuthoxy aluminum, diphenylmethoxy aluminum, diphenylcyclohexyloxy aluminum, dioctyldibutoxy aluminum, methyldiethoxy aluminum, ethyldimethoxy aluminum, isobutyldibutoxy aluminum, and the like.

(3) Oxygen-containing or oxygenated compounds (C)

One group of compounds in the oxygenated compounds according to the present invention are carbonyl compounds having the general formula (a)

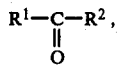

wherein $R^1$ is a member selected from the group consisting of $C_1$–$C_{10}$ alkyl, aryl, and aralkyl radicals, and $R^2$ is a member selected from the group consisting of hydrogen atom, $C_1$–$C_{10}$ alkyl, ary, aralkyl radicals which may be the same as or different from $R^1$, and $OR^3$ groups where $R^3$ is a radical selected from the group consisting of $C_1$–$C_{10}$ alkyl, aryl, and aralkyl. $R^1$ may combine with $R^2$ to form a cyclic structure containing —CO— radical where total $R^1+R^2$ carbon atoms may be approximately 3 to 7, inclusive, in view of the stability of the cyclic structure thereof. Accordingly, the carbonyl compounds mentioned above relate to ketones, aldehydes, and esters, respectively.

Another group of compounds in the oxygenated compounds of the invention are ether compounds having the general formula (b) $R^4$—O—$R^5$, where $R^4$ and $R^5$ each represents a member selected from the group consisting of $C_1$–$C_{10}$ alkyl, aryl, and aralkyl radicals. $R^4$ and $R^5$ may be combined with each other to form a cyclic ether, where total $R^4+R^5$ carbon atoms may be approximately 3 to 7, inclusive.

Each oxygenated compound (C) may be used after the formation of each corresponding complex with a titanium compound and a succeeding stabilization therefor, or such an oxygenated compound may also be mixed with the other components at the time of preparing the catalyst.

Specific examples of the oxygenated compounds as mentioned above according to the present invention are aromatic aldehydes, benzaldehyde; mono-substituted benzaldehydes such as o-, m-, p-chlorobenzaldehydes, o-, m-, p-fluorobenzaldehydes, o-, m-, p-bromobenzaldehydes, o-, m-, p-cyanobenzaldehydes, o-, m-, p-formylbenzaldehydes, o-, m-, p-nitrobenzaldehydes, o-, m-, p-trifluoromethylbenzaldehydes, o-, m-, p-sulfonamidebenzaldehydes, o-, m-, p-phenylbenzaldehydes, o-, m-, p-formylbenzisocyanates, o-, m-, p-methoxybenzaldehydes, o-, m-, p-ethoxybenzaldehydes, and o-, m-, p-butoxybenzaldehydes; di-substituted benzaldehydes such as 2, 3-dichlorobenzaldehyde, 2, 4-dichlorobenzaldehyde, 2, 5-dichlorobenzaldehyde, 2, 6-dichlorobenzaldehyde, 3, 4-dichlorobenzaldehyde, 3, 5-dichlorobenzaldehyde, 3, 6-dichlorobenzaldehyde, 2-chloro-3-nitrobenzaldehyde, 2-chloro-4-nitrobenzaldehyde, 2-chloro-5-nitrobenzaldehyde, 2-chloro-6-nitrobenzaldehyde, 3-chloro-2-nitrobenzaldehyde, 3-chloro-4-nitrobenzaldehyde, 4-chloro-2-nitrobenzaldehyde, 4-chloro-3-nitrobenzaldehyde, 2-nitro-3-chlorobenzaldehyde, and 2-nitro-4-chlorobenzaldehyde; tri-substituted benzaldehydes such as 2, 3, 4-trichlorobenzaldehyde, 2, 3, 5-trichlorobenzaldehyde, 2, 3, 6-trichlorobenzaldehyde, 2, 4, 5-trichlorobenzaldehyde, 2, 4, 6-trichlorobenzaldehyde, 3, 4, 5-trichlorobenzaldehyde, 2, 3-dichloro-4-nitrobenzaldehyde, 2, 4-dichloro-3-nitrobenzaldehyde, 3-chloro-4-trifluoromethyl-5-nitrobenzaldehyde, and 2-chloro-4-cyano-5-formyl-benzaldehyde; and poly-substituted benzaldehydes such as 2, 3, 4, 5-tetrachlorobenzaldehyde, 2, 3, 4, 6-tetrachlorobenzaldehyde, pentachlorobenzaldehyde, 3, 4, 5-trichloro-2-nitrobenzaldehyde, 3, 4, 6-trichloro-5-nitrobenzaldehyde, 4-cyano-2, 3, 6-trichlorobenzaldehyde, and tetrachloroterephthaladehyde.

Furthermore, aldehydes such as α- and β-naphthylaldehydes and their substituted derivatives and polycyclic benzaldehydes are also effective for the oxygenated compounds in the present invention. In addition to the above, aliphatic and alicyclic aldehydes are also effective for the present invention as the oxygenated compounds. Specific examples thereof are n-butylaldehyde, n-, isooctylaldehydes, 2-ethylhexylaldehyde, acrolein, 1-pentenylaldehyde, cyclohexylaldehyde, 1-cyclohexenylaldehyde, 1-, 2-decalinaldehydes, and their substituted derivatives. Carboxylic esters which are effective for the process according to the present invention are methyl benzoate, ethyl benzoate, butyl benzoate, 2-ethylhexyl benzoate, octyl benzoate, phenyl benzoate, benzyl benzoate, methyl acetate, ethyl acetate, butyl acetate, octyl acetate, methyl proprionate, butyl propionate, phenyl propionate, and the like. Specific examples of ketones are acetone, methyl ethyl ketone, diethyl ketone, dibutyl ketone, anisole, diphenyl ketone, methylcyclohexyl ketone, cyclohexanone, and the like.

There are, as specific examples of ethers used in the present invention, diethyl ether, dibutyl ether, diisoamyl ether, ethylene glycol diethyl ether, ethylene glycol dibutyl ether, dioxane, trioxane, trimethyl trioxane, tetrahydrofuran, furfural, and the like.

Among the oxygenated compounds mentioned above, aldehydes and ketones are particularly preferable. Furthermore, the benzaldehydes and their substituted compounds are preferable as the aldehydes in the present invention, and in this case, substitutents having high electro-negativity in the substituted compounds as well as substituted positions thereof which are 2-, 4-, and 6-positions are preferable. Examples are nitro, cyano, formyl, halogen, trifluoromethyl, benzyl, methylsulfinyl, methylsulfonyl, and benzoyloxy substitutents.

(4) Sulfur-containing compounds or nitrile compounds (D)

One group of these compounds are sulfur-containing compounds having the general formula

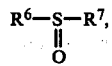

where $R^6$ and $R^7$ each represents a member selected from the group consisting of approximately $C_1$–$C_{10}$ alkyl which can contain a thioether bond, aryl, and aralkyl radicals. $R^6$ and $R^7$ may be combined with each other to form a cyclic sulfoxide containing —SO— radical, where total $R^6+R^7$ carbon atoms may be approximately 3 to 7, inclusive.

As specific examples of the sulfur-containing compounds of the present invention, there are dimethyl sulfoxide, dipropyl sulfoxide, diphenyl sulfoxide, tetramethylene sulfoxide, formaldehyde dimethyl mercaptyl-S-oxide, and the like.

Another group of the compounds (D) are compounds having the general formula Y—$R^8$—Y', where Y and Y' each represents a member selected from the group consisting of CN, SCN, and $SR^9$ radicals wherein $R_9$ is selected from the group consisting of $C_1$–$C_{10}$ alkyl, aryl, and aralkyl radicals, and $R^8$ is selected from the group conconsisting of —(CH$_2$)$_n$— (n being an integer having a value of 1-10),

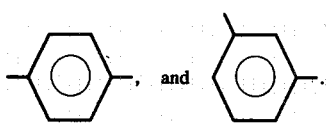

Examples of Y=Y'=CN radicals are adiponitrile, glutaronitrile, succinonitrile, malononitrile, terephthalnitrile, and the like.

Specific examples of Y=Y'=SCN radicals are ethane-1, 2-dithiocyanato, propane-1, 3-dithiocyanato, butane-1, 4-dithiocyanato, and the like. There are 1,2-diethylthio-ethane, 1, 3-diethylthiopropane, and the like as specific examples of Y=Y'=SR radicals in the nitrile compounds according to the present invention.

(5) Composition of catalyst

The quantity of the titanium compound according to the present invention with respect to that of monomeric isoprene (IP) is preferably within a range of from 0.00005 to 0.1 in Ti/IP (mol ratio) and more preferably within a range of from 0.0001 to 0.01.

Regarding quantities of the oxygenated compound (C) as well as the sulfur-containing compound or the nitrile compound (D) of the present invention with respect to the titanium compound, the compound (C)/the compound (A) (Ti) (mol ratio) is preferably in a range of from 0.1 to 10 and more preferably in a range of from 0.5 to 3, while the compound (D)/the compound (A) (Ti) (mol ratio) is preferably within a range of from 0.5 to 5 and more preferably within a range of from 0.5 to 1. In this case, the quantitative relation between the compounds (C) and (D) is important, and if the balance of this quantitative relation is lost, the activity of the catalyst will deteriorate.

Furthermore, as for the quantity of the organoaluminum compound (compound (B)) (Al) of the present invention with respect to the titanium compound (the compound (Al)), the Al/Ti (mol ratio) is preferably in the range of from 0.5 to 100 and more preferably within the range of from 1 to 20.

(6) Preparation of catalyst

The catalyst according to the present invention is prepared by admixing the respective components as mentioned above with each other in an atmosphere of an inert gas such as nitrogen or argon.

The order of mixing the respective components is not a matter of great importance, but such process steps as described hereinbelow are preferable. That is, the titanium compound (A) is introduced into a solvent, then, the oxygenated compound (C) as well as the sulfur-containing compound or the nitrile compound (D) are also introduced thereinto, and the mixture thus obtained is caused to react for approximately 0.5 to 1 hour. Thereafter, the organoaluminum compound (B) is added to the resultant reaction product, whereby highly effective catalyst is produced which permits a continuous oligomerization and has a high activity as well as a high selectivity can be obtained. The organoaluminum compound may be added after the introduction of isoprene if so desired. The temperature in the preparation of the catalyst is preferably within a range of from 0 to 100° C.

2. Oligomerization

It is preferable to carry out oligomerization of isoprene in a solvent.

It is preferable that the solvent be the one which has been preliminarily subjected to dehydration and degasification is preferable, but a solvent without dehydration and deaeration may also be employed if it has been treated beforehand with the organoaluminum compound herein used as a catalyst.

Various hydrocarbon solvents such as aliphatic, alicyclic, and aromatic solvents can be used in the oligomerization according to the present invention.

In general, the reaction conditions for the oligomerization are as follows.

Temperature: Within a range of from room temperature to 150° C., and preferably within a range of from 50° C. to 100° C.

Pressure: Atmospheric pressure or the autogenous pressure of the system, and generally within a range of from 1 to 5 kg/cm$^2$ Gauge.

3. Structures of products

Products prepared by the process according to the present invention are cyclic trimers of isoprene, and more particularly trimethylcyclododecatriene-(1, 5, 9) in which methyl radicals are positioned at 1, 6, 9-position as well as 1, 5, 9-position, respectively.

4. Experimental examples

The yield mentioned hereinbelow is indicated by % by weight of the quantity of the product with respect to 68 g (1 mol) of the charged monomer, and the selectivity of the product is indicated by % by weight of the quantity of cyclic oligomer in the resultant trimers.

In these experiments, all the reactions were carried out at a temperature of 65° C. for 3 hours, and 100 ml of toluene was employed as a solvent in each case.

Example 1

100 ml of toluene, which had been preliminarily subjected to dehydration and deaeration, was introduced into a Widmer flask of 300 ml capacity in which the air therein had been previously replaced with argon gas. Then, 0.077 g (0.5 millimol) of titanium trichloride manufactured by Toho Titanium Co., Japan, under trade name "TAC", 0.093 g (0.5 millimol) of 2-chloro-5-nitrobenzaldehyde, 0.018 ml (0.25 millimol) of dimethyl sulfoxide, 0.48 ml (3.5 millimol) of diethylaluminum chloride, and 100 ml (1 mol) isoprene were successively introduced into the flask to obtain a solution. The resulting solution was further introduced into a stainless steel autoclave having 500 ml capacity and provided with an induction stirrer, and the temperature of the solution was elevated to 65° C., and then maintained thereat for 3 hours thereby to carry out the oligomerization.

Then 2 ml of methanol was added to the mass discharged from the autoclave thereby to decompose the catalyst. Thereafter, products were separated by distillation.

As a result, 13.6 g (yield 20%) of an isoprene dimer fraction was obtained in a boiling point range of from 160° to 180° C., and, further, 39.3 g of a trimer fraction was obtained in a boiling point range of from 90° to 110° C. under a reduced pressure of 2 mm Hg which was found upon gas chromatography to contain 1.2 g of a linear trimer and 38.1 g (yield 56% and selectivity 97% in the trimers) of a cyclic trimer (trimethylcyclododecatriene).

No higher polymer adherent to the reaction vessel was found in this example.

Examples 2-21 and Reference Examples 1-4

Other experiments were carried out similarly as in Example 1.

The reaction conditions and results were as indicated in the following Tables 1 and 2, respectively. Among Al-species in these Tables, DEAC and EASC represent AlEt$_2$Cl and AlEt$_{1.5}$Cl$_{1.5}$, respectively. The unit of quantity mM means millimol. The degree with which adherent higher polymer is produced is indicated in these Tables as follows. O indicates no production of such adherent higher polymer; X indicates there is some production of adhesive polymer; and XX indicates remarkable production of the adherent polymer. Furthermore, in the Tables, symbols Me, Et, Bu, $\phi$, and DMSO represent methyl, ethyl, butyl, phenyl, and dimethyl sulfoxide, respectively.

Table 1

| Example No. | Ti-species (A) Type | Ti-species (A) Quantity (mM) | Al-species (B) Type | Al-species (B) Quantity (mM) | Additive (C) Type | Additive (C) Quantity (mM) | Additive (D) Type | Additive (D) Quantity (mM) | Dimer Yield (g) | Linear Product Yield (g) | Trimer Cyclic Product Yield (g) | Trimer Cyclic product Yield (%) | Cyclic product selectivity (%) | Degree of production of adherent higher polymer |
|---|---|---|---|---|---|---|---|---|---|---|---|---|---|---|
| 2 | TiCl₃ | 0.5 | DEAC | 3.5 | C₆H₅–CHO | 0.5 | DMSO | 0.25 | 11.6 | 2.9 | 32.6 | 48 | 92 | 0 |
| 3 | " | " | " | " | 4-NO₂–C₆H₄–CHO | " | " | " | 17.7 | 1.6 | 30.0 | 44 | 95 | 0 |
| 4 | " | " | " | 2 | 4-Cl–C₆H₄–CHO | " | " | " | 15.4 | 2.8 | 32.0 | 47 | 92 | 0 |
| 5 | " | " | " | " | C₆H₄(CHO)₂ | " | " | " | 15.1 | 2.0 | 38.1 | 56 | 95 | 0 |
| 6 | " | " | " | " | 4-OMe–C₆H₄–CHO | 0.8 | " | " | 23.2 | 2.9 | 28.3 | 42 | 91 | 0 |
| 7 | " | " | " | 3.5 | 3,4-Cl₂–C₆H₃–CHO | 0.5 | " | 0.65 | 13.8 | 2.8 | 38.9 | 57 | 93 | 0 |

Table 1-continued

| Example No. | Ti-species (A) Type | Quantity (mM) | Al-species (B) Type | Quantity (mM) | Additive (C) Type | Quantity (mM) | (D) Type | Quantity (mM) | Dimer Yield (g) | Linear Product Yield (g) | Trimer Cyclic Product Yield (g) | Yield (%) | Cyclic product selectivity (%) | Degree of production of adherent higher polymer |
|---|---|---|---|---|---|---|---|---|---|---|---|---|---|---|
| 8 | " | " | " | " | 2,4-Cl₂-C₆H₃-CHO | " | " | " | 18.4 | 2.6 | 34.7 | 51 | 93 | 0 |
| 9 | " | " | " | " | 3,5-Cl₂-4-NO₂-C₆H₂-CHO | 1.5 | " | 0.35 | 11.7 | 1.2 | 43.5 | 64 | 97 | 0 |
| 10 | " | " | " | " | C₃—C≡C—CHO | 1 | " | " | 19.9 | 2.5 | 33.4 | 49 | 93 | 0 |
| 11 | " | " | " | " | (C₆H₅)₂C=O | 0.5 | " | " | 19.1 | 2.3 | 35.4 | 52 | 94 | 0 |
| 12 | " | " | EASC | 5.0 | p-COOEt-C₆H₄ | " | " | " | 9.5 | 1.1 | 27.9 | 41 | 96 | 0 |
| 13 | " | " | " | 3.5 | 1,3,5-trioxane | " | " | " | 12.9 | 1.8 | 41.8 | 61 | 96 | 0 |
| 14 | " | " | DEAC | 7.5 | 2-Br-6-φ-C₆H₃-CHO | " | NCS—C₂—SCN | 0.25 | 18.2 | 2.6 | 35.2 | 52 | 93 | 0 |

Table 1-continued

| Example No. | Ti-species (A) Type | Ti-species (A) Quantity (mM) | Al-species (B) Type | Al-species (B) Quantity (mM) | Additive (C) Type | Additive (C) Quantity (mM) | Additive (D) Type | Additive (D) Quantity (mM) | Dimer Yield (g) | Linear Product Yield (g) | Trimer Cyclic product Yield (g) | Trimer Cyclic product Yield (%) | Cyclic product selectivity (%) | Degree of production of adherent higher polymer |
|---|---|---|---|---|---|---|---|---|---|---|---|---|---|---|
| 15 | " | " | " | 4.0 | ⌬-Br | 0.25 | NC-⌬-CN | 0.25 | 17.6 | 0.9 | 30.7 | 45 | 97 | 0 |
| 16 | TiCl₃·CHO-⌬-DMSO | " | " | 5 | — | — | — | — | 10.8 | 2.6 | 33.2 | 49 | 93 | 0 |
| 17 | TiCl₃₂ CHO-⌬-CHO | 0.4 | " | 6 | DMSO | 0.2 | — | — | 13.9 | 2.2 | 39.2 | 58 | 95 | 0 |
| 18 | TiCl₃ | 0.5 | " | 3.5 | Bu—CHO CHO ⌬-NO₂ | 0.5 | DMSO | 0.25 | 20.5 | 2.7 | 32.8 | 48 | 92 | 0 |
| 19 | " | " | " | " | " | " | " | " | 10.5 | 2.2 | 31.9 | 47 | 94 | 0 |
| 20 | " | " | " | " | Et—C—Et ‖ O | " | " | " | 17.8 | 2.6 | 33.7 | 49 | 94 | 0 |
| 21 | " | " | " | " | C₅H₁₁—O—C₅H₁₁ | " | " | " | 9.8 | 2.1 | 29.3 | 43 | 93 | 0 |

Table 2

| Reference Ex. No. | Ti-species Type | Ti-species Quantity (mM) | Al-species Type | Al-species Quantity (mM) | Additive 1 Type | Additive 1 Quantity (mM) | Additive 2 Type | Additive 2 Quantity (mM) | Dimer Yield (g) | Trimer Linear product Yield (g) | Trimer Cyclic product Yield (g) | Cyclic product selectivity (%) | Degree of production of adherent higher polymer |
|---|---|---|---|---|---|---|---|---|---|---|---|---|---|
| 1 | TiCl$_4$ | 0.5 | DEAC | 2.0 | CHO 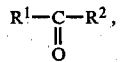 | 0.5 | — | — | 19.7 | 2.8 | 25.2 | 37 | 90 | X |
| 2 | TiCl$_3$ | " | " | 3.5 | — | — | — | — | 8.9 | 4.1 | 12.3 | 18 | 75 | X |
| 3 | " | 0.6 | " | 4.2 | NMe$_3$ | 0.6 | DMSO | 0.3 | 43.5 | 4.8 | 7.5 | 11 | 61 | O |
| 4 | " | " | " | " | AlCl$_3$ | " | ψ—O—ψ  | " | 5.8 | 3.6 | 5.8 | 9 | 62 | XX |

What is claimed is:

1. A process for producing isoprene cyclic trimers which comprises catalytically oligomerizing isoprene to produce trimethylcyclododecatriene, by contacting said isoprene at a temperature of about room temperature to about 150° C. with a catalyst consisting essentially of a combination of:

(A) a tri-valent titanium compound;
(B) an organoaluminum compound;
(C) an oxygen-containing compound selected from the group consisting of:
 (a) a carbonyl compound having the formula $$R^1-\underset{\underset{O}{\|}}{C}-R^2,$$

wherein $R^1$ is a member selected from the group consisting of $C_1$–$C_{10}$ alkyl, aryl, and aralkyl radicals; $R^2$ is a member selected from the group consisting of hydrogen, $C_1$–$C_{10}$ alkyl, aryl, aralkyl, and $OR^3$ groups wherein $R^3$ is a member selected from the group consisting of $C_1$–$C_{10}$ alkyl, aryl, and aralkyl radicals; and $R^1$ and $R^2$ may be combined with each other to form a cyclic structure, and (b) an ether compound having the formula $$R^4-O-R^5,$$

where $R^4$ and $R^5$ each represents a member selected from the group consisting of $C_1$–$C_{10}$ alkyl, aryl, and aralkyl radicals; and $R^4$ and $R^5$ may be combined with each other to form a cyclic structure; and (D) a compound selected from the group consisting of:
 (a) a sulfur-containing compound having the formula $$R^6-\underset{\underset{O}{\|}}{S}-R^7,$$

where $R^6$ and $R^7$ each represents a member selected from the group consisting of hydrogen, $C_1$–$C_{10}$ alkyl which can contain a thioether bond in its chain, aryl, and aralkyl radicals; and $R^6$ and $R^7$ may be combined with each other to form a cyclic structure, and (b) a compound having the following formula $$Y-R^8-Y',$$

where Y and Y' each represents a member selected from the group consisting of CN, SCN, and $SR^9$ radicals wherein $R^9$ is a member selected from the group consisting of $C_1$–$C_{10}$ alkyl, aryl, and aralkyl radicals; and $R^8$ is a member selected from the group consisting of —$(CH_2)_n$— wherein n is an integer having a value of 1–10, inclusive,

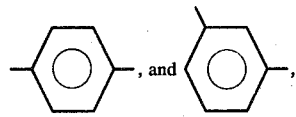

wherein the mole ratio of compound (C)/compound (A) is about 0.1 to 10 and the mole ratio of compound (D)/compound (A) is about 0.5 to 5.

2. A process as claimed in claim 1 wherein said tri-valent titanium compound is a tri-valent titanium halogen compound.

3. A process as claimed in claim 2 wherein said tri-valent titanium halogen compound is in the form of mixed crystals consisting essentially of a titanium trihalide and an aluminum trihalide.

4. A process as claimed in claims 1, 2 or 3 wherein said organoaluminum compound is an aluminum compound having the general formula $$AlR_nX_{3-n},$$

where R is a member selected from the group consisting of hydrogen, $C_1$–$C_{12}$ alkyl, aryl, and aralkyl radicals; X is a member selected from the group consisting of halogen atoms and OR' radicals wherein R' is a member selected from the group consisting of $C_1$–$C_{12}$ alkyl, aryl, and aralkyl radicals; and n is a number selected from the values of 1, 1.5, 2, and 3.

5. A process as claimed in claims 1, 2 or 3 wherein said carbonyl compound is a compound selected from the group consisting of aldehydes, ketones, and carboxylic esters.

6. A process as claimed in claims 1, 2 or 3 where the proportions in mole ratio between compounds (A) and (B) is as follows:

$$\frac{\text{the compound }(B)}{\text{the compound }(A)} : \text{from 0.5 to 100}.$$

7. A process as claimed in claims 1, 2 or 3 under a pressure of from 1 to 5 kg/cm$^2$ Gauge.

* * * * *